United States Patent
Merkel et al.

(10) Patent No.: US 8,519,201 B2
(45) Date of Patent: Aug. 27, 2013

(54) PROCESS FOR SEPARATING HYDROGEN FLUORIDE FROM ORGANIC FEEDSTOCKS

(75) Inventors: Daniel C. Merkel, Orchard Park, NY (US); Konstantin A. Pokrovski, Orchard Park, NY (US); Hsueh S. Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/423,726

(22) Filed: Mar. 19, 2012

(65) Prior Publication Data

US 2012/0190901 A1 Jul. 26, 2012

Related U.S. Application Data

(62) Division of application No. 12/464,666, filed on May 12, 2009, now Pat. No. 8,168,837.

(60) Provisional application No. 61/053,518, filed on May 15, 2008.

(51) Int. Cl.
*C07C 17/38* (2006.01)
*C07C 17/00* (2006.01)

(52) U.S. Cl.
USPC ............................ 570/177; 570/161

(58) Field of Classification Search
USPC .................................. 570/161, 177
See application file for complete search history.

(56) References Cited

U.S. PATENT DOCUMENTS

| | | |
|---|---|---|
| 5,918,481 A | 7/1999 | Pham et al. |
| 2006/0106263 A1 | 5/2006 | Miller et al. |
| 2007/0100175 A1 | 5/2007 | Miller et al. |
| 2007/0197842 A1 | 8/2007 | Mukhopadhyay et al. |
| 2008/0030615 A1 | 2/2008 | Vasquez et al. |

FOREIGN PATENT DOCUMENTS

| | | |
|---|---|---|
| EP | 2080748 A2 | 7/2009 |
| WO | 2008024508 A1 | 2/2008 |

OTHER PUBLICATIONS

Kim, et al., "A Study to Determine the Existence of an Azeotropic R-22 "Drop-In" Substitute," prepared by U.S. Department of Commerce for Electric Power Research Institute, Mar. 1996, pp. 1-45, U.S.
Morrison, et al., "Azeotropy in Refrigerant Mixtures," International Journal of Refrigeration, 1993, pp. 129-138, vol. 16, No. 2. U.S.

*Primary Examiner* — Jafar Parsa
(74) *Attorney, Agent, or Firm* — Bruce O. Bradford

(57) ABSTRACT

Provided is a process for purifying an organic feedstock comprising (a) distilling a raw organic feedstock comprising hydrogen fluoride, 2-chloro-1,1,1,2-tetrafluoropropane, and 2-chloro-3,3,3-trifluoropropene to produce a first distillate stream comprising an azeotrope-like composition of 2-chloro-1,1,1,2-tetrafluoropropane, 2-chloro-3,3,3-trifluoropropene, and hydrogen fluoride, and a first bottoms stream rich in hydrogen fluoride; (b) cooling said first distillate stream to produce an intermediate composition comprising an organic layer rich in 2-chloro-1,1,1,2-tetrafluoropropane and 2-chloro-3,3,3-trifluoropropene, and an acid layer rich in hydrogen fluoride; and, optionally but preferably, (c) distilling said organic layer to produce a second distillate stream comprising an azeotrope-like composition of 2-chloro-1,1,1, 2-tetrafluoropropane, 2-chloro-3,3,3-trifluoropropene, and hydrogen fluoride, and a second bottoms stream comprising a purified organic feedstock substantially free of hydrogen fluoride.

8 Claims, 2 Drawing Sheets

US 8,519,201 B2

PROCESS FOR SEPARATING HYDROGEN FLUORIDE FROM ORGANIC FEEDSTOCKS

CROSS-REFERENCE TO RELATED APPLICATIONS

This application is a divisional application of U.S. application Ser. No. 12/464,666, filed May 12, 2009 (now U.S. Pat. No. 8,168,837), which claims the priority benefit of US Provisional Application No. 61/053,518, filed May 15, 2008, both of which are incorporated herein by reference.

BACKGROUND

1. Field of the Invention

This invention relates to a process for separating components of an azeotrope-like mixture. More particularly, this invention relates to a process for separating hydrogen fluoride from an azeotrope-like mixture comprising hydrogen fluoride and at least one hydrofluorocarbon.

2. Description of Prior Art

Certain hydrofluoroolefins, such as 2,3,3,3-tetrafluoropropene (HFO-1234yf), are useful in a variety of applications. For example, HFO-1234yf can be used as a refrigerant, solvent, blowing agent, and the like. Hydrofluoroolefins have a relatively low Global Warming Potential (GWP) and little or no ozone depletion potential. Therefore, these compounds are environmentally friendly.

HFO-1234yf can be manufactured from 1,1,2,3-tetrachloropropene or 1,1,1,2,3-pentachloropropane using a multi-step process, such as the one described in US Publication No. 2007/0197842. One part of this process involves dehydrochlorinating 2-chloro-1,1,1,2-tetrafluoropropane (HCFC-244bb) to form the desired HFO-1234yf. The HCFC-244bb, in turn, can be obtained by reacting 2-chloro-3,3,3-trifluoropropene (HCFO-1233xf) with a stoichiometric excess of hydrogen fluoride (HF). The excess HF in the reaction mixture optimizes the conversion of HCFO-1233xf and the selectivity of the desired HCFC-244bb product. However, due to this excess HF and limitations in the reaction's efficiency, the resulting reaction product typically contains un-reacted HCFO-1233xf as well as a significant amount of unreacted HF. Preferably, the unreacted HF is recovered from the reaction product and recycled to increase the economic efficiency of the process.

SUMMARY OF THE INVENTION

This invention is directed, in part, to a novel process for separating HF from a mixture of HF, HCFO-1233xf, and HCFC-244bb.

As noted above, the reaction of HCFO-1233xf with excess HF produces a reaction product comprising HCFC-244bb, unreacted HF, and unreacted HCFO-1233xf. Inventors have found that the presence of HF is detrimental to a reaction process in which HCFC-244bb is dehydrochlorinated to form HFO-1234yf. Thus, to be useful as a starting material in the synthesis of HFO-1234yf, a feedstock of HCFC-244bb is preferably substantially free of HF.

However, separation of HF from this crude reaction product is difficult via standard distillation techniques because HF forms a binary azeotrope-like composition with both HCFC-244bb and HCFO-1233xf individually, and also forms a ternary azeotrope-like composition with HCFC-244bb and HCFO-1233xf. Simply recycling the entire azeotrope-like fraction though the HCFC-244bb synthesis reaction is uneconomical because it would involve reprocessing large amounts of the desired product. This reprocessing would require additional reactor capacity and use more energy, thus increasing capital and operational costs.

Inventors have discovered a method for separating HF from a mixture of HF, HCFO-1233xf, and HCFC-244bb that involves one or more distillations and at least one phase separation, the integration of which unexpectedly achieves an HF stream containing very little organic compounds and an HCFC-244bb/HCFO-1233xf stream containing very little HF.

More particularly, the binary and ternary azeotrope-like compositions formed between HF and HCFC-244bb and/or HCFO-1233xf have a boiling point lower than any of the components individually and, as such, these azeotrope-like compositions can be at least partially separated from non-azeotropic mixtures of these compounds. In addition, the inventors have found that these azeotrope-like compositions are heterogeneous at certain concentrations of hydrogen fluoride and at certain temperatures (e.g., about −30° C. to about +10° C.). Accordingly, at least a portion of the components of the azeotrope-like compositions can be separated from the azeotrope-like composition in a phase-separation vessel by reducing the temperature of the azeotrope-like composition.

Therefore, an aspect of the present invention provides a process for purifying an organic feedstock comprising (a) distilling a raw organic feedstock comprising hydrogen fluoride, 2-chloro-1,1,1,2-tetrafluoropropane, and 2-chloro-3,3,3-trifluoropropene to produce a first distillate stream comprising an azeotrope-like composition of 2-chloro-1,1,1,2-tetrafluoropropane, 2-chloro-3,3,3-trifluoropropene, and hydrogen fluoride, and a first bottoms stream rich in hydrogen fluoride; (b) cooling said first distillate stream to produce an intermediate composition comprising an organic layer rich in 2-chloro-1,1,1,2-tetrafluoropropane and 2-chloro-3,3,3-trifluoropropene, and an acid layer rich in hydrogen fluoride; and, optionally but preferably, (c) distilling said organic layer to produce a second distillate stream comprising an azeotrope-like composition of 2-chloro-1,1,1,2-tetrafluoropropane, 2-chloro-3,3,3-trifluoropropene, and hydrogen fluoride, and a second bottoms stream comprising a purified organic feedstock substantially free of hydrogen fluoride.

In another aspect, provided is a process for preparing 2-chloro-1,1,1,2-tetrafluoropropane comprising (a) reacting a first feed stream comprising 2-chloro-3,3,3-trifluoropropene with a second feed stream comprising hydrogen fluoride, and optionally with one or more recycle streams comprising hydrogen fluoride, to produce a crude product stream comprising 2-chloro-1,1,1,2-tetrafluoropropane, hydrogen fluoride, and 2-chloro-3,3,3-trifluoropropene; (b) distilling said crude product stream to produce a first distillate stream comprising an azeotrope-like composition of 2-chloro-1,1,1,2-tetrafluoropropane, 2-chloro-3,3,3-trifluoropropene, and hydrogen fluoride, and a first bottoms stream rich in hydrogen fluoride; (c) cooling said first distillate stream to produce an intermediate composition comprising an organic layer rich in 2-chloro-1,1,1,2-tetrafluoropropane and 2-chloro-3,3,3-trifluoropropene, and an acid layer rich in hydrogen fluoride; and, optionally but preferably, (d) distilling said organic layer to produce a second distillate stream comprising an azeotrope-like composition of 2-chloro-1,1,1,2-tetrafluoropropane, 2-chloro-3,3,3-trifluoropropene, and hydrogen fluoride, and a second bottoms stream comprising an organic composition rich in 2-chloro-1,1,1,2-tetrafluoropropane and substantially free of hydrogen fluoride.

In yet another aspect of the invention, provided is a process for producing 2,3,3,3-tetrafluoropropene comprising (a) reacting 2-chloro-3,3,3-trifluoropropene with hydrogen fluoride to produce a crude product stream comprising 2-chloro-1,1,1,2-tetrafluoropropane, hydrogen fluoride, and 2-chloro-3,3,3-trifluoropropene; (b) distilling said crude product stream to produce a first distillate stream comprising an azeotrope-like composition of 2-chloro-1,1,1,2-tetrafluoropropane, 2-chloro-3,3,3-trifluoropropene, and hydrogen fluoride, and a first bottoms stream rich in hydrogen fluoride; (c) cooling said distillate stream to produce a first intermediate composition comprising an organic layer rich in 2-chloro-1,1,1,2-tetrafluoropropane and 2-chloro-3,3,3-trifluoropropene, and an acid layer rich in hydrogen fluoride; (d) distilling said organic layer to produce a second distillate stream comprising an azeotrope-like composition of 2-chloro-1,1,1,2-tetrafluoropropane, 2-chloro-3,3,3-trifluoropropene, and hydrogen fluoride, and a second bottoms stream comprising a second intermediate composition rich in 2-chloro-1,1,1,2-tetrafluoropropane and substantially free of hydrogen fluoride; and (e) dehydrochlorinating at least a portion of 2-chloro-1,1,1,2-tetrafluoropropane in said second intermediate composition to produce a final product comprising 2,3,3,3-tetrafluoropropene.

DETAILED DESCRIPTION OF PREFERRED EMBODIMENTS OF THE INVENTION

Figure 1:
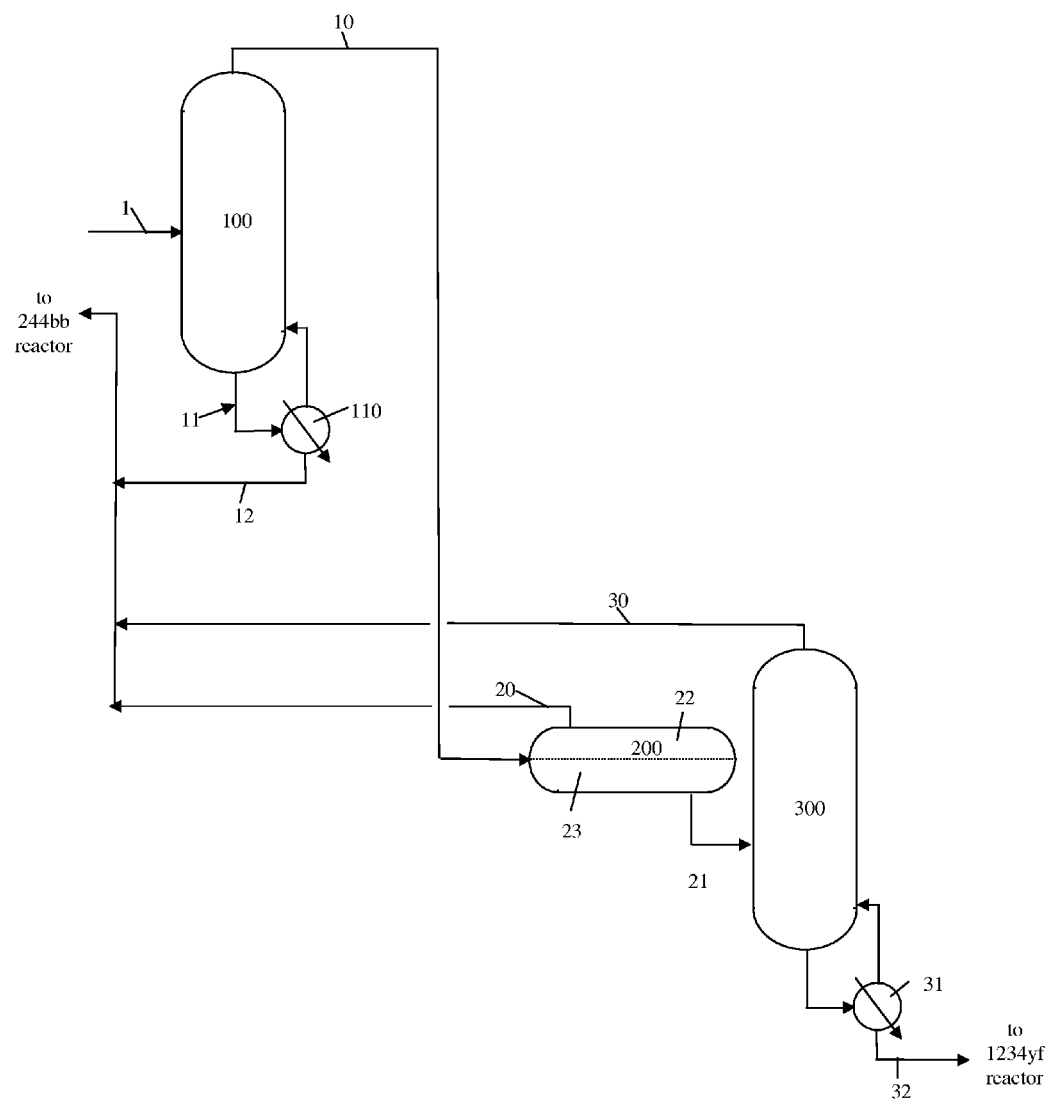
FIG. 1 is a process flow diagram showing a preferred embodiment of the invention.
Figure 2:
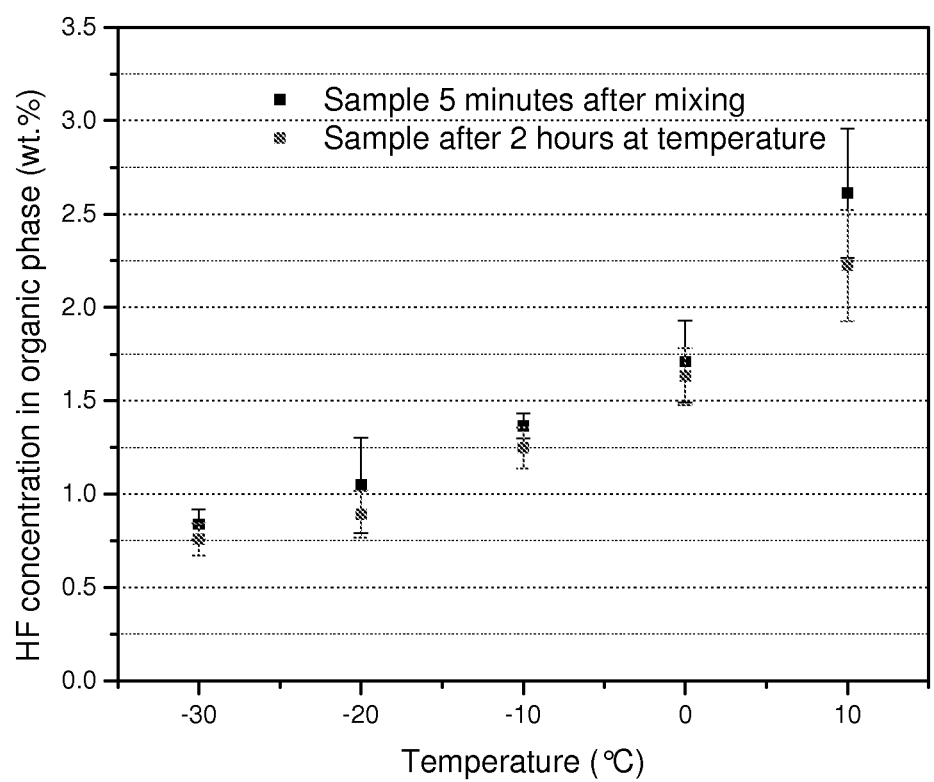
FIG. 2 is a graphical depiction of data from Example 2 showing the concentration of HF in the organic phase of the phase separation vessel as a function of temperature.

Referring to FIG. 1, shown is a process flow diagram according to a preferred embodiment of the invention wherein HF is separated from a crude process stream 1 comprising HF, HCFC-244bb, and HCFO-1233xf to produce a purified organic stream 32 substantially free of HF. Product stream 1 contains about 60-70 wt % HF and the balance organic (primarily HCFC-244bb and HCFO-1233xf). Preferably, this stream comprises the product of a reaction involving the fluorination of HCFO-1233xf with excess HF to produce HCFC-244bb. At least a portion of the HCFC-244bb, HCFO-1233xf, and HF in product stream 1 are in the form of one or more azeotrope-like mixtures, that is azeotrope-like mixtures consisting essentially of HF and HCFC-244bb, azeotrope-like mixtures consisting essentially of HF and HCFO-1233xf, and/or azeotrope-like mixtures consisting essentially of HF, HCFC-244bb, and HCFO-1233xf.

As used herein, the term "azeotrope-like" relates to compositions that are strictly azeotropic or that generally behave like azeotropic mixtures. An azeotropic mixture is a system of two or more components in which the liquid composition and vapor composition are equal at the stated pressure and temperature. In practice, this means that the components of an azeotropic mixture are constant-boiling or essentially constant-boiling and generally cannot be thermodynamically separated during a phase change. The vapor composition formed by boiling or evaporation of an azeotropic mixture is identical, or substantially identical, to the original liquid composition. Thus, the concentration of components in the liquid and vapor phases of azeotrope-like compositions change only minimally, if at all, as the composition boils or otherwise evaporates. In contrast, boiling or evaporating non-azeotropic mixtures changes the component concentrations in the liquid phase to a significant degree.

As used herein, the term "consisting essentially of", with respect to the components of an azeotrope-like composition, means the composition contains the indicated components in an azeotrope-like ratio, and may contain additional components provided that the additional components do not form new azeotrope-like systems. For example, azeotrope-like mixtures consisting essentially of two compounds are those that form binary azeotropes, which optionally may include one or more additional components, provided that the additional components do not render the mixture non-azeotropic and do not form an azeotrope with either or both of the compounds.

As used herein, the term "essentially free of hydrogen fluoride" with respect to a composition means that the composition comprises no more than 1 weight percent hydrogen fluoride.

According to a preferred embodiment, crude process stream 1 is distilled via a conventional distillation column 100 to produce a distillate stream 10 and a bottoms stream 11. Since the HF/HCFO-1233xf, HF/HCFC-244bb, and HF/HCFO-1233xf/HCFC-244bb azeotrope-like compositions are lower boiling than a majority of the pure components and because HF is present in excess of azeotropic amounts, the distillate material 10 taken from the column overhead is rich in organics, e.g., about 20 to about 30 wt. % HF and from about 70 to about 80 wt. % organics. Nearly pure HF (e.g., >99 wt. %) is taken from the reboiler 10 as a bottom stream 12, which is preferably recycled back to the HCFC-244bb reactor (not shown).

The distillate stream 10 from the first distillation column 100 is fed into a phase separation vessel 200. Preferably, the distillate stream is cooled to a temperature of about +10° C. to about −30° C., more preferably to a temperature of about −10° C. to about −30° C. either prior to entering or within the phase separation vessel 200. Taking advantage of the heterogeneous property of the azeotrope-like composition, the mixture can be readily separated into 2 distinct layers, an upper layer 22 rich in HF (acid layer) and a bottom layer 23 rich in organic (organic layer). It has been found that cooling the mixture enhances the phase separation.

The acid layer 22, which is rich in HF, also contains about 10 to about 20 wt. % of organics. This layer can be separated from the organic layer and recycled 20 back to the HCFC-244bb reactor (not shown).

The organic layer 23 typically contains less than about 3 wt. % HF. This layer can be separated from the acid layer as a feed stream 21 to a second distillation column 300. Here, the 1233xf/244bb/HF azeotrope-like compositions will be removed from the top of the column as distillate material 30. Nearly pure organic 1233xf/244bb (e.g., at least about 99 wt. %) 32 is taken from the reboiler 310 bottom and, optionally, is fed forward for a subsequent HFO-1234yf synthesis process. Overall, there is nearly a 100% recovery of HF for recycle back to the HCFC-244bb reactor.

EXAMPLES

Example 1

This example demonstrates the efficacy of the first distillation operation according to the present invention.

Approximately 100 lbs of reactor effluent from a vapor phase reaction of 1233xf+HF→244bb were charged to a distillation column. The distillation column consisted of a 10 gallon reboiler, 2 inch ID by 8 feet propack column, and a shell and tube condenser. The column had about 30 theoretical plates. The distillation column was equipped with temperature, pressure, and differential pressure transmitters. The composition of the material was about 70 wt. % HF and 30 wt. % organic (mixture of mainly HCFO-1233xf and HCFC-244bb). A distillation was performed at about 100 psig pressure to recover the organic. In total, 38 lbs of distillate was collected which included about 20-30 wt. % HF. The balance was organic having an average GC analysis of 55% HCFO-1233xf and 45% HCFC-244bb. The reboiler bottoms were drained to a separate cylinder and 62 lbs of mainly HF were recovered.

Example 2

This example demonstrates the separation efficacy of the liquid-liquid phase separation operation according to the present invention.

The phase separator feed is a mixture of HF, HCFO-1233xf, and HCFC-244bb. The separation of organic and HF layers was tested in the temperature range from about +10° C. to about −30° C. The highest concentration of HF in the organic layer was detected at +10° C. (2.23±0.30 wt. %), the lowest concentration of HF in the organic layer was detected at −30° C. (0.76±0.09 wt. %). The concentration of HF in the HF layer was about 90±5 wt. %. GC analysis of organic and HF layers indicated that there is no difference in the organic composition between organic and HF layer.

The phase-separation of the mixture containing HCFC-244bb, HCFO-1233xf, and HF was performed in the temperature range of −30° C. to +10° C. A 500 ml SS sample cylinder was used for the study. The temperature of the cylinder was controlled with ethanol circulating through the coil wrapped around the cylinder. A thermocouple was attached to the outside wall of the cylinder (between cooling coil and the cylinder wall) and positioned in the middle of the cylinder to measure the temperature. The cylinder was also equipped with sampling valves at the bottom and the top of the cylinder. To the cylinder was charged 98.7 g of anhydrous HF and 233 g of a 93.0 GC area % 244bb/5.0 GC area % 1233xf mixture. The weight ratio HF:Organic was about 29.8:70.2. The cylinder was padded with nitrogen to 12 psig at −30° C. to allow sampling. Samples were taken from the bottom of the cylinder into Tedlar gas sample bags that contained 5 grams of distilled water for the purpose of absorbing HF. The first sample was taken two hours after the cylinder reached the desired temperature. After this, the contents of the cylinder were mixed and a second sample was taken five minutes after mixing. HF concentration was determined by titration with 0.1 N KOH of the aqueous phase of the sample bags. HF concentrations in the samples of the bottom (organic) phase taken after equilibrating the contents of the phase-separator for 2 hours at given temperature are presented in Table 1. HF concentration in samples of the bottom (organic) phase taken 5 minutes after mixing contents of the cylinder at given temperature is presented in Table 2.

HF concentration in the HF layer was analyzed after the organic layer was removed from the system. KOH titration showed that concentration of HF in the acid layer was about 90±5%. The distribution of organics in the HF layer was the same as in the organics layer.

TABLE 1

| Temperature (° C.) | HF concentration in bottom (organic) phase (wt. %) | Standard deviation |
|---|---|---|
| −30 | 0.76 | 0.09 |

TABLE 1-continued

| Temperature (° C.) | HF concentration in bottom (organic) phase (wt. %) | Standard deviation |
|---|---|---|
| −20 | 0.89 | 0.13 |
| −10 | 1.25 | 0.11 |
| 0 | 1.63 | 0.15 |
| 10 | 2.23 | 0.30 |

TABLE 2

| Temperature (° C.) | HF concentration in bottom (organic) phase (wt. %) | Standard deviation |
|---|---|---|
| −30 | 0.84 | 0.08 |
| −20 | 1.05 | 0.26 |
| −10 | 1.37 | 0.07 |
| 0 | 1.71 | 0.22 |
| 10 | 2.61 | 0.35 |

Example 3

This example demonstrates the separation efficacy of the second distillation operation according to the present invention.

The distillation column feed was a mixture of HF, 1233xf, and 244bb. Approximately 37.4 pounds of the material containing 3 weight percent HF balanced with mixture of organics consisting of 44.4 weight percent HCFC-244bb and 55.6 weight percent HCFO-1233xf was charged into the distillation column. The mixture was homogeneous. The distillation column consisted of a 10 gallon reboiler, 2 inch ID by 8 feet propack column, and a shell and tube condenser. The column had about 30 theoretical plates. The distillation column was equipped with temperature, pressure, and differential pressure transmitters. The distillation was run at a pressure of about 23-25 psig. The distillate was sampled, titrated for HF concentration determination, and analyzed by GC at regular intervals.

Analysis showed a ternary azeotrope of HF/HCFC-244bb/HCFO-1233xf. The HF concentration of the azeotrope was analyzed to be about 25-33 wt. % HF using titration with 0.1 N KOH. The organic concentration based on GC area % was about 17-21 GC area % HCFC-244bb and about 79-83 GC area % HCFO-1233xf. At a pressure of 23-25 psig the column overhead temperature was about 23° C. for this composition.

Example 4

This example also demonstrates the separation efficacy of the second distillation operation according to the present invention.

The distillation column feed is a mixture of HF, 1233xf, and 244bb. For this example, a Monel distillation column was used which consisted of two liter reboiler, 1 inch ID×4 feet helicoil packed column, and tube and shell condenser. The column was equipped with temperature, pressure, and differential pressure transmitters. Approximately 1000 grams of material containing about 3.2 wt. % HF balanced with mixture of organics consisting of about 51 weight percent HCFC-244bb and 49 weight percent HCFO-1233xf were charged into the distillation system. The mixture was homogeneous. The distillation was performed at a pressure of 7-29 psig. Analysis of distillate samples showed consistent results at a pressure above 18 psig. The organic composition by GC was determined to be about 21-23 GC Area % HCFC-244bb and about 79-77 GC Area % HCFO-1233xf and the concentration of HF in the distillate was found to be about 25-29 weight % HF using titration with 0.1 N NaOH. The decrease in the amount of HF in the sample occurred sharply indicating a ternary azeotrope of HCFC-244bb/HCFO-1233xf/HF.

Example 5

This example shows a calculated material balance for the 3 step integrated HF recovery process according to one embodiment of the invention.

Reaction: HCFO-1233xf+HF→HCFC-244bb

The basis and assumptions for the calculation are: 100 lbs of reactor effluent (i.e., the composition of feed into the first distillation column (HF Recovery Step 1 feed) is 65 lbs HF, 35 lbs organics (i.e., mixture of 1233xf/244bb)); the mole ratio of HF to organic that is fed to the reactor is 20:1; the wt. % of HF in the organic layer after step 2 (phase separation) of the HF recovery process is 2%; and the wt. % of organic in the HF layer after step 2 (phase separation) of the HF recovery process is 15%. Table 3 shows the material balance for all 3 steps of the HF recovery process.

TABLE 3

| Distillation | | Phase Separation | | Distillation | |
|---|---|---|---|---|---|
| Step 1 Distillate (lbs) | Step 1 Bottoms (lbs) | Step 2 HF layer (lbs) | Step 2 org. layer (lbs) | Step 3 Distillate (lbs) | Step 3 Bottoms (lbs) |
| 15 | 50 | 14.34 | 0.66 | 0.66 | 0 |
| 35 | 0 | 2.53 | 32.47 | 1.55 | 30.92 |

| | lbs | % | |
|---|---|---|---|
| HF Recovery | 65 | 100 | recycle to 2nd step reactor |
| Organic Recovery | 30.9 | 88.4 | forward to next reaction step |

Having thus described a few particular embodiments of the invention, it will be apparent to those skilled in the art, in view of the teachings contained herein, that various alterations, modifications, and improvements not specifically described are available and within the scope of the present invention. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A process for preparing 2-chloro-1,1,1,2-tetrafluoropropane comprising:

a. reacting a first feed stream comprising 2-chloro-3,3,3-trifluoropropene with a second feed stream comprising hydrogen fluoride, and optionally with one or more recycle streams comprising hydrogen fluoride, to produce a crude product stream comprising 2-chloro-1,1,1,2-tetrafluoropropane, hydrogen fluoride, and 2-chloro-3,3,3-trifluoropropene;

b. distilling said crude product stream to produce a first distillate stream comprising an azeotrope-like composition of 2-chloro-1,1,1,2-tetrafluoropropane, 2-chloro-3,3,3-trifluoropropene, and hydrogen fluoride, and a first bottoms stream rich in hydrogen fluoride; and c. cooling said first distillate stream to produce an intermediate composition comprising an organic layer rich in 2-chloro-1,1,1,2-tetrafluoropropane and 2-chloro-3,3,3-trifluoropropene, and an acid layer rich in hydrogen fluoride.

2. The process of claim 1 further comprising d. distilling said organic layer to produce a second distillate stream comprising an azeotrope-like composition of 2-chloro-1,1,1,2-tetrafluoropropane, 2-chloro-3,3,3-trifluoropropene, and hydrogen fluoride, and a second bottoms stream comprising an organic composition rich in 2-chloro-1,1,1,2-tetrafluoropropane and substantially free of hydrogen fluoride.

3. The process of claim 2 wherein said cooling produces a first distillate stream having a temperature of about −30° C. to about +10° C.

4. The process of claim 3 wherein said second bottoms stream comprises at least about 80 weight percent of the combined mass of said 2-chloro-1,1,1,2-tetrafluoropropane and 2-chloro-3,3,3-trifluoropropene in said crude product stream.

5. The process of claim 4 wherein said crude product stream comprises about 60 to about 70 weight percent hydrogen fluoride.

6. The process of claim 5 further comprising reboiling said first bottoms stream to produce a first recycle stream comprising at least about 95 weight percent hydrogen fluoride, wherein said first recycle stream is combined with said second feed stream prior to step (a) and/or is introduced into step (a) as said one or more recycle streams.

7. The process of claim 5 further comprising combining said acid layer with said second feed stream prior to step (a) and/or introducing said acid layer into step (a) as said one or more recycle streams, wherein said acid layer comprises at least about 80 weight percent hydrogen fluoride.

8. The process of claim 5 further comprising combining said second distillate stream with said second feed stream prior to step (a) and/or introducing said acid layer into step (a) as said one or more recycle streams.

* * * * *